(12) United States Patent
Hamet et al.

(10) Patent No.: US 7,045,124 B1
(45) Date of Patent: May 16, 2006

(54) PRE-CONDITIONING AGAINST CELL DEATH

(75) Inventors: Pavel Hamet, Montreal (CA);
Johannes Tremblay, Montreal (CA);
Christine Desrosier, Montreal (CA);
Huifang Chen, Pointe-Claire (CA)

(73) Assignee: Vasogen Irelend Limited (IE)

( * ) Notice: Subject to any disclaimer, the term of this patent is extended or adjusted under 35 U.S.C. 154(b) by 0 days.

(21) Appl. No.: 09/480,260

(22) Filed: Jan. 11, 2000

Related U.S. Application Data

(60) Provisional application No. 60/115,636, filed on Jan. 12, 1999.

(51) Int. Cl.
*A01N 63/00* (2006.01)

(52) U.S. Cl. .................................... 424/93.7
(58) Field of Classification Search ............... 424/93.7, 424/613
See application file for complete search history.

(56) References Cited

U.S. PATENT DOCUMENTS 5,591,457 A * 1/1997 Bolton ........................ 424/613
5,834,030 A * 11/1998 Bolton ........................ 424/613
6,136,308 A * 10/2000 Tremblay et al. ........... 424/93.7

FOREIGN PATENT DOCUMENTS

WO  WO 99/13890  3/1999

WO  WO 00/67764  11/2000

OTHER PUBLICATIONS

Ganelina et al., "Therapy of Severe Steno Cardias by UV Irradiation of the Blood and Some Action Mechanisms of This Therapy", Folia Haematologica, DE, Akademische Verlagsgesellschaft, Leipzig, vol. 109, No. 3, 1982, pp. 470-482, Abstract Only.

Cooke, et al., "Treatment of severe Raynaud's syndrome by injection of autologous blood pretreated by heating, ozonation and exposure to ultraviolet light (H-O-U) therapy", International Angiology, Dec. 1997, pp. 250-254, United Kingdom.

* cited by examiner

*Primary Examiner*—Michael Meller
(74) *Attorney, Agent, or Firm*—Foley & Lardner LLP

(57) ABSTRACT

Apoptosis and/or necrosis related disorders in the mammalian body, namely radiation exposure disorders, chemical exposure and ingestion disorders, neurological disorders and physical trauma disorders, are treated, and their onset is counteracted by preconditioning, by extracting from the mammalian body an aliquot of blood, subjecting the extracted aliquot, ex vivo, to an oxidative stressor such as exposure to ozone gas, a temperature stressor, i.e. temperatures above or below body temperatures, and ultraviolet light, and re-injecting the treated blood aliquot into the mammalian body. The treatment ha the effect of decreasing apoptosis/necrosis in the body, and of pre-conditioning the body better to withstand subsequently encountered apoptosis-inducing events.

11 Claims, 4 Drawing Sheets

PRE-CONDITIONING AGAINST CELL DEATH

This application claims the benefit of U.S. Provisional Application No. 60/115,636, filed Jan. 12, 1999, the entire content of which is hereby incorporated by reference in this application.

FIELD OF THE INVENTION

This invention relates to the field of medicine. More specifically, the invention relates to means for pre-conditioning the mammalian body, including the human body, so as to enable cellular organs thereof better to resist subsequently encountered cell death as induced by apoptosis-inducing events, or by necrosis-inducing events, including events inducing both apoptosis and necrosis.

BACKGROUND OF THE INVENTION

The two known forms of cellular death are necrosis and apoptosis. Apoptosis is the biological process of controlled, programmed cell death, by means of which cells die by a process of condensation without the release of cell contents into the surrounding milieu. Cells of most organs and tissues divide and multiply over time, a process that is normally in equilibrium with cell death by apoptosis, resulting in optimal cell numbers in the healthy body, Apoptosis, therefore, can be considered to act as a control on the total number of cells in organs and tissues. Residues of apoptosed cells are largely consumed by other cells, by a process of phagocytosis. The process of apoptosis, the natural, well-regulated process by which the body undertakes removal of unwanted cells is to be contrasted with the process of necrosis by which the cells die largely in an uncontrolled manner, as a result of membrane rupture. Importantly, however, in many instances apoptosis and necrosis behave as a continuum. The intracellular components of necrosed cells are released into the organism in an uncontrolled manner, commonly resulting in inflammatory reactions as the body attempts to deal with these suddenly encountered components. Apoptosed cells cause virtually no harmful inflammatory reactions.

Some medical disorders in a living body, or an individual organ of a living body, can be attributed at least in part to an undue acceleration in the rate of apoptosis. This can occur, for example, when a body ingests chemical poisons or encounters excessive amounts of harmful radiation (radioactivity, UV exposure, etc.). Other disorders involve both apoptosis and necrosis. Still other disorders involve an accelerated rate of cell death due primarily to necrosis.

Apoptosis of the cell is understood to be initiated by an alteration in the functioning of the mitochondria of the cell. Mitochondria, as is well known, are membrane-bounded organelles, located within the cell, and occupying a major fraction of the total cell volume. They contain large amounts of internal membrane. The main function of mitochondria is to convert energy from foodstuffs to forms that can be used to drive cellular reactions. This is accomplished by a process of chemiosmotic coupling, by which membrane-bound ion pumps transfer ions from one side of the mitochondrial membrane to the other. The proton pumps generate an electrochemical proton gradient across the membrane, which is used to drive various energy-requiring reactions when the protons flow through membrane embedded proteins such as the enzyme ATP synthase. As an ionic process, the potential across the mitochondrial membrane is important in the efficient operation of this energy-providing mechanism. Mitochondria participate directly in the induction of apoptosis by releasing pro-apoptotic proteins. Decreases in mitochondrial membrane potential are known to be indicative of the commencement of apoptosis.

Organs undergoing apoptosis exhibit oligonucleosomal DNA fragmentation into 180–200 base pairs, in a specific pattern which appears as a ladder after gel electrophoresis. The degree of DNA fragmentation correlates with the progression of apoptosis in the organ, and can be measured by extracting the DNA, radiolabelling it, subjecting it to electrophoresis and quantifying the radioactivity associated with various DNA fragments. Such techniques can be used to determine the numbers of cells undergoing apoptosis or exhibiting an apoptotic condition or predisposition, so as to determine an extent or degree of apoptosis in a body organ or tissue.

In the course of necrosis, enzymes and other cell contents normally contained in the cytoplasm are released, as a result of disintegration of cell membranes, a hallmark of necrosis. One of these is the enzyme lactate dehydrogenase (LDH), the levels of which are commonly used to determine the degree of necrosis.

BRIEF REFERENCE TO THE PRIOR ART

U.S. Pat. No. 4,968,483 Mueller et al. describes an apparatus for oxygenating blood, by treating an aliquot of a patient's blood extracorporeally, with an oxygen/ozone mixture and ultraviolet light, at a controlled temperature. The apparatus is proposed for use in hematological oxidation therapy.

U.S. Pat. No. 5,591,457 Bolton, discloses a method of inhibiting the aggregation of blood platelets in a human, a method of stimulating the immune system and a method of treating peripheral vascular diseases such as Raynaud's disease, by extracting an aliquot of blood from a patient, subjecting it to ozone/oxygen gas mixture, and ultraviolet radiation at a temperature in the range of about 37–43° C., and then reinjecting the treated blood in the human patient.

U.S. Pat. No. 5,834,030 Bolton, describes a similar process for increasing the content of nitric oxide in the blood of a mammalian patient, potentially useful in treating conditions such as high blood pressure in mammalian patients.

International Patent Application PCT/CA97/00564 Vasogen Inc. (WO98/07436) described an autoimmune vaccine for administration to human patients to alleviate the symptoms of autoimmune diseases such as rheumatoid arthritis, the vaccine comprises an aliquot of the patient's blood which has been subjected extracorporeally to an oxidizing environment UV radiation and elevated temperature.

It is an object of the present invention to provide means for pre-conditioning a mammalian patient to better withstand external cellular insults likely to effect acceleration of or to increase the degree of apoptosis in tissues or organs of the mammalian patient.

It is a further object of the invention to provide means for preconditioning a mammalian patient to better withstand external cellular insults likely to effect acceleration of or increase the degree of necrosis in tissues or organs of the patient.

It is a further object of the invention to provide a pre-conditioning process for mammalian patients against the harmful effects of chemical and radiation poisoning.

It is a further object of the invention to provide a process for alleviating or decelerating the progression of the symptoms of apoptosis-related or necrosis-related medical disorders.

SUMMARY OF THE INVENTION

The present invention provides a process whereby a mammalian body may be preconditioned so that the cells of organs and tissues can better resist subsequently encountered apoptosis- and/or necrosis-inducing events. The process involves in vitro treatment of an aliquot of the blood from the mammalian body, with certain stressors to effect modification of the blood aliquot. Then the treated blood aliquot is reintroduced into the mammalian body. The result is a significant increase in resistance to apoptosis and apoptosis/necrosis of the cells of the body, as indicated by changes in mitochrondrial membrane potential, decrease of DNA laddering, and decrease of release of LDH, when the cells are subsequently exposed to stressing or toxic agents.

The aliquot of blood is treated by being subjected to one or more stressors which have been found to modify he blood. According to the present invention, the blood aliquot can be modified by subjecting the blood, or separated cellular or non-cellular fractions of the blood, or mixtures of the separated cells and/or non-cellular fractions of the blood, to stressors selected from heat, ultraviolet light and oxidizing environments. The stressors may be applied individually, or in any combination of two or more of such stressors, simultaneously or sequentially.

Accordingly, the process of the invention may be used for pre-conditioning the mammalian body against the effects of a wide range of subsequently encountered factors known to cause pathological conditions which are associated with excessive degrees of apoptosis or necrosis of cells of various body organs.

Medical disorders associated with excessive degrees of apoptosis and/or necrosis in various organs or tissues, and for which, accordingly, the process of the present invention is indicated for use, either as a treatment thereof or as preconditioning against the effects thereof, can be classified into four general categories. These are:

(1) radiation exposure disorders, which include exposure to excessive amounts of ionizing, radiation such as nuclear radiation, therapeutic radiation or X-rays; or ultraviolet light (resulting in skin disorders such as sunburn, for example). The fact that such radiation exposure disorders are associated with increases in apoptosis is known, for example from Blankenberg et. al. "Dying a thousand deaths. Radionuclide imaging of apoptosis", *O.J. Nucl. Med.* 1999 June; 43(2): 170–6 and various references cited therein; from Wong, G. H. "Protective roles of cytokines against radiation: induction of mitochondrial MnSOD", *Biochim. Biophys. Acta* 1995 May 24; 1271(1): 205–209 and various references cited therein, from Zhao et al. "Mitochondrial and intracellular free-calcium regulation of radiation-induced apoptosis in human leukemic cells", *Int J Radiat Biol* 1999 April; 75(4): 493–504; and from Reap E. A. et.al., "Radiation and stress-induced apoptosis: a role for Fas/Fas ligand interactions", *Proc Natl Acad Sci USA.* 1997 May 27; 94(11):5750–5

(2) chemical exposure and ingestion disorders, which include chemical poisoning; food poisoning from bacterial toxins; toxic drug ingestion overdoses and side effects; disorders from exposure to chemical warfare agents such as nerve gases and mustard gas; liver disorders from chemicals and toxins (including alcohol); kidney disorders e.g. resulting from ingestion of aminoglycoside antibiotics, radiographic contrast dyes or cyclosporin nephrotoxicity; hematopoietic disorders and immunodeficiency disorders derived from drug or toxin induced bone marrow suppression; infections from bacterial toxins; ozone exposure; solvent exposure; and the effects of immunosuppressants such as cyclosporin, cyclophosphamide or azathioprine. The fact that such chemical ingestion and exposure disorders are associated with increases in apoptosis is known, for example from Losser M R and Payen D, "Mechanisms of liver damage", *Semin Liver Dis* 1996 November; 16(4): 357–67; from Smith K. J. et. al., Immunohistochemical studies of basement membrane proteins and proliferation and apoptosis markers in sulfur mustard induced cutaneous lesions in weanling pigs", *J. Dermaol. Sci.*, 1997 September; 15(3): 173–82; from Dabrowska M. I. et. al., Sulfur mustard induces apoptosis and necrosis in endothelial cells", *Toxicol Appl Pharmacol* 1966 December; 141(2): 569–83; from Muller et. al., "Anthracycline-derived chemotherapeutics in apoptosis and free radical cytotoxicity (Review)", Int J Mol Med 1998 February: 1(2): 491–4, and various references cited therein; from Healey et. al., "Apoptosis and necrosis: mechanisms of cell death induced by cyclosporine A in a renal proximal tubular cell line", *Kidney Int,* 1998 December; 54(6): 1955–66; from Hatake K et.al., "Apoptosis-gene expression in hematopoietic system normal and pathological conditions (Review)", *Int J Mol Med* 1998 January; 1(1): 121–9 and various references cited therein; from Banker D. E. et. al., "Measurement of spontaneous and therapeutic agent-induced apoptosis with BCL-2 protein expression in acute myeloid leukemia", *Blood,* 1997 Jan. 1;(1):243–55; from Voetberg B. J. et. al., "Apoptosis accompanies a change in the phenotypic . . . ", *Clin Immunol Immunopathol* 1994 May; 71(2): 190–8; and from Mountz J. D. et. al. "Autoimmune disease. A problem of defective apoptosis", *Arthritis Rheum* 1994 October; 37(10): 1415–20;

(3) neurological disorders such as Parkinson's disease (which involves apoptosis of specific brain cells), senile dementia, and Alzheimer's disease and like diseases: The fact that such neurological disorders are associated with increases in apoptosis is known, for example from Desjardins P. Ledoux "The role of apoptosis in neurodegenerative diseases," *Metab. Brain Dis.* 1998 June; 13(2):79–96; from Dragunow M, McGibbon G. A. et.al. "Apoptosis, neurotrophic factors and neurodegeneration", *Rev. Neurosci.* 1997 July–December;8(3–4): 223–265; from Kitamura Y, Taniguchi T, Shimohama S, "Apoptotic cell death in neurons and glial cells: implications for Alzheimer's disease", *Jpn J. Pharmacol.* 1999 January; 79(1): 1–5; and from Budd S. L. and Nicholls D. G. "Mitochondria in the life and death of neurons", *Essays Biochem* 1998;33;43–52; and other publications both preceding and following those detailed above;

(4) physical trauma disorders such as physical accident injuries, wounding, thermal injuries (burns), and losses of blood such as occur during surgery. The fact that such disorders are associated with increases in apoptosis is known, for example from Wilson S. E, "Molecular cell biology for the refractive corneal surgeon: programmed cell death and wound healing", *J Refract Surg.* 1997 March–April; 13(2): 171–5.

The determination of whether or not a particular process or procedure has an effect on apoptosis in tissues or organs of the living mammalian body is best determined at the cellular level, e.g. by determination of mitochondrial membrane potential or by determination of the degree of DNA fragmentation. These measurements are described in more detail in the specific examples which follow. A determination by such measurements that a process or procedure leads to a decrease in apoptosis is an indication that such a process or procedure is effective in treating or preconditioning against any of the apoptosis related disorders listed in the four categories above. Such a determination of apoptosis inhibiting effects of a process or procedure, at the cellular level, in conjunction with a demonstrated efficacy of that process in alleviating or preconditioning against a disorder in one of the above categories is strong evidence of potential clinical success of that process or procedure in alleviating or preconditioning against other disorders in the same category.

Thus the process of the invention is primarily indicated for use by people who are likely to encounter conditions where they are exposed to such factors, such as workers in chemical manufacturing facilities, nuclear installations and the like, or physically hazardous situations such as emergency response teams. Potential military applications whereby troops may be preconditioned against a wide variety of hazards, will be apparent. More specific indications for use of the process are in connection with patients undergoing medical treatments, including administration of toxic drugs, which are accompanied by undesired side effects. For example, the administration of immunosuppressants such as cyclosporin, cyclophosphamide and azathioprine to assist in organ transplants and for other purposes leads commonly to apoptosis and/or necrosis acceleration associated disorders. The use of the process of the present invention on patients involved in such treatments can be beneficial, particularly since the treatment regimen for such patients, both with drugs or radiation and with the process of the invention, can be carefully planned in advance and conducted according to a carefully controlled schedule.

In addition to the use of the process of the invention, to pre-condition a body or body organ against subsequently encountered factors, the process can also be used to control or to alleviate the symptoms of a medical disorder involving increased apoptosis and/or necrosis. The term "alleviating or protecting against the symptoms" as used herein refers to both pre-conditioning to afford protection, and treatment of manifested symptoms. In situations where the causative factor of the medical disorder is associated with ageing (Parkinson's disease or senile dementia, for example), use of the process of the invention by patients suffering from the disorder, in order to control it or to alleviate its symptoms, is the most practical use of it. Indeed, clinical tests have provided evidence of improvement in cognition and general well-being of elderly patients.

Accordingly, in one aspect the present invention provides a process of alleviating or protecting against the symptoms of a medical disorder involving accelerated rates of apoptosis or necrosis in a mammalian body, said disorder being selected from radiation exposure disorders; chemical exposure and ingestion disorders; neurological disorders; and physical trauma disorders; which comprises reducing the rate of or susceptibility to apoptosis or necrosis of tissues and organs of the mammalian body by (a) reacting an aliquot of blood from the mammalian body ex vivo with at least one stressor selected from the group consisting of a temperature above or below body temperature, ultraviolet light, and an oxidative environment; and (b) administering the aliquot of blood treated in step (a) to the mammalian body.

DESCRIPTION OF THE PREFERRED EMBODIMENTS

Figure 1:
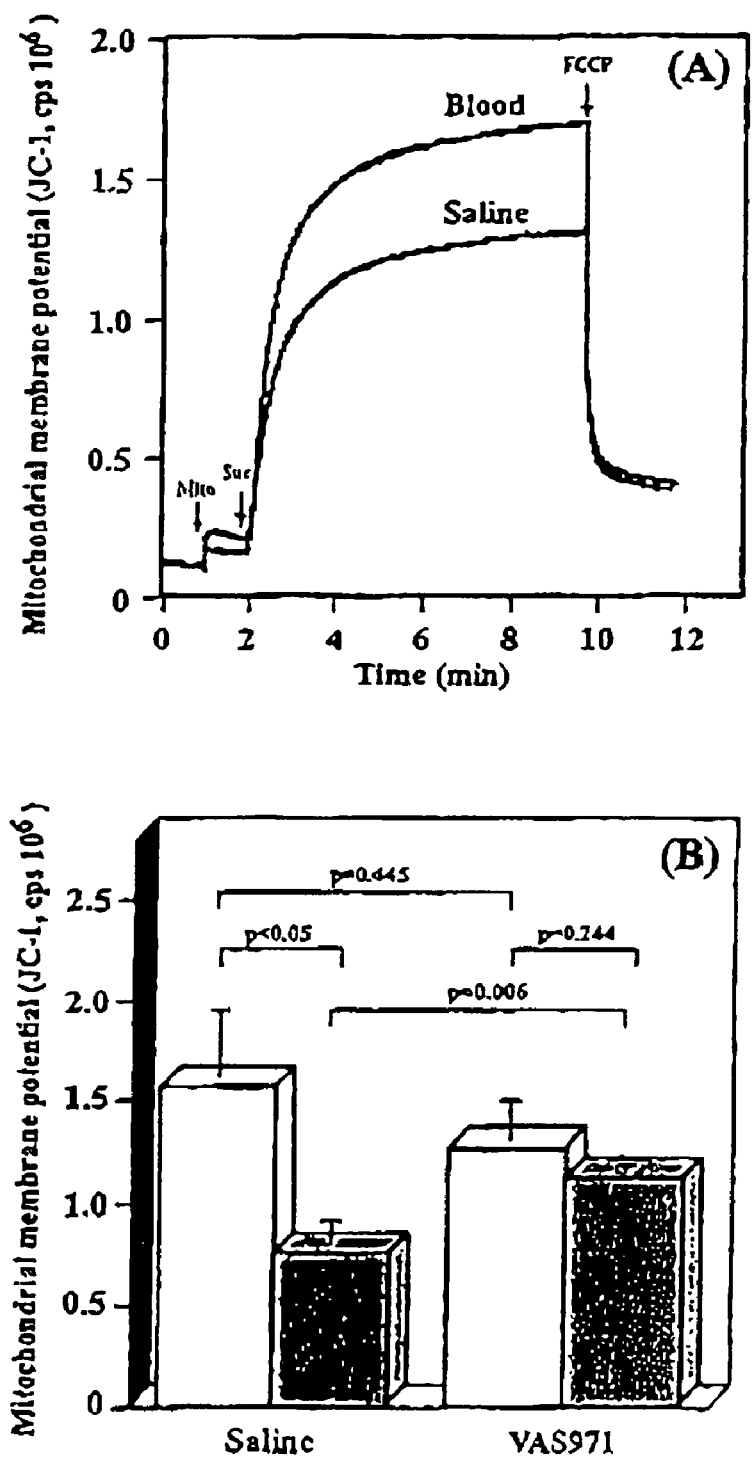
FIG. 1 of the accompanying drawings is a graphical presentation of the results obtained from Example 1 described below.

According to a preferred process of the present invention, an aliquot of blood is extracted from a mammalian subject, preferably a human, and the aliquot of blood is treated ex vivo with certain stressors, described in more detail below. The terms "aliquot", "aliquot of blood" or similar terms used herein include whole blood, separated cellular fractions of the blood including platelets, separated non-cellular fractions of the blood including plasma, and combinations thereof. The effect of the stressors is to modify the blood, and/or the cellular or non-cellular fractions thereof, contained in the aliquot. The modified aliquot is then re-introduced into the subject's body by any suitable method, most preferably intramuscular injection, but also including subcutaneous injection, intraperitoneal injection, and oral, nasal or rectal administration, intra-arterial injection or intravenous injection.

The stressors to which the aliquot of blood is subjected ex vivo according to the method of the present invention are selected from temperature stress (blood temperature above or below body temperature), an oxidative environment and ultraviolet light, individually or in any combination, simultaneously or sequentially. The aliquot has a volume sufficient that, when re-introduced into the subject's body, a pre-conditioning against apoptosis level is achieved in the subject. Preferably, in human patients, the volume of the aliquot is up to about 400 ml, preferably from about 0.1 to about 100 ml, more preferably from about 5 to about 15 ml, even more preferably from about 8 to about 12 ml, and most preferably about 10 ml.

It is preferred, according to the invention, to apply all three of the aforementioned stressors simultaneously to the aliquot under treatment, in order to ensure the appropriate modification to the blood. It may also be preferred in some embodiments of the invention to apply any two of the above stressors, for example to apply temperature stress and oxidative stress, temperature stress and ultraviolet light, or ultraviolet light and oxidative stress. Care must be taken to utilize an appropriate level of the stressors to thereby effectively modify the blood to achieve the desired effect.

The temperature stressor warms the aliquot being treated to a temperature above normal body temperature or cools the aliquot below normal body temperature. The temperature is selected so that the temperature stressor does not cause excessive hemolysis in the blood contained in the aliquot and so that, when the treated aliquot is injected into a subject, an effective preconditioning against apoptosis and/or necrosis will be achieved. Preferably, the temperature stressor is applied so that the temperature of all or a part of the aliquot is up to about 55° C., and more preferably in the range of from about −5° C. to about 55° C.

In some preferred embodiments of the invention, the temperature of the aliquot is raised above normal body temperature, such that the mean temperature of the aliquot does not exceed a temperature of about 55° C., more preferably from about 40° C. to about 50° C., even more preferably from about 40° C. to about 44° C., and most preferably about 42.5±1° C.

In other preferred embodiments, the aliquot is cooled below normal body temperature such that the mean temperature of the aliquot is within the range of from about 4° C. to about 36.5° C., even more preferably from about 10° C. to about 30° C., and even more preferably from about 15° C. to about 25° C.

The oxidative environment stressor can be the application to the aliquot of solid, liquid or gaseous oxidizing agents. Preferably, it involves exposing the aliquot to a mixture of medical grade oxygen and ozone gas, most preferably by bubbling through the aliquot, at the aforementioned temperature range, a stream of medical grade oxygen gas having ozone as a minor component therein. The ozone content of the gas stream and the flow rate of the gas stream are preferably selected such that the amount of ozone introduced to the blood aliquot, either on its own or in combination with other stressors, does not give rise to excessive levels of cell damage. Suitably, the gas stream has an ozone content of up to about 300 μg/ml, preferably from about 10 to about 100 μg/ml, more preferably about 30 μg/ml, even more preferably up to about 20 μg/ml, particularly preferably from about 10 μg/ml to about 20 μg/ml, and most preferably about 14.5±1.0 μg/ml. The gas stream is suitably supplied to the aliquot at a rate of up to about 2.0 liters/min, preferably up to about 0.5 liters/min, more preferably up to about 0.4 liters/min, even more preferably up to about 0.33 liters/min, and most preferably about 0.24±0.024 liters/min. The lower limit of the flow rate of the gas stream is preferably not lower than 0.01 liters/min, more preferably not lower than 0.1 liters/min, and even more preferably not lower than 0.2 liters/min.

The ultraviolet light stressor is suitably applied by irradiating the aliquot under treatment from a source of UV light while the aliquot is maintained at the aforementioned temperature and while the oxygen/ozone gaseous mixture is being bubbled through the aliquot Preferred UV sources are UV lamps emitting UV-C band wavelengths, i.e. at wavelengths shorter than about 280 nm. Ultraviolet light corresponding to standard UV-A (wavelengths from about 315 to about 400 nm) and UV-B (wavelengths from about 280 to about 315) sources can also be used. For example, an appropriate dosage of such UV light, applied simultaneously with the aforementioned temperature and oxidative environment stressors, can be obtained from lamps with a power consumption of from about 15 to about 30 watts and useful UV output of about 5–10 watts, arranged to surround the sample container holding the aliquot. Up to eight such lamps surrounding the sample bottle, operated at an intensity to deliver a total UV light energy at 253.7 nm at the surface of the blood of from about 0.025 to about 10 joules/cm$^2$, preferably from about 0.1 to about 3.0 joules/cm$^2$, may advantageously be used. Such a treatment provides a modified blood aliquot which is ready for injection into the subject.

The time for which the aliquot is subjected to the stressors is normally within the time range from about 0.5 up to about 60 minutes. The time depends to some extent upon the chosen intensity of the UV light, the temperature, the concentration of the oxidizing agent and the rate at which it is supplied to the aliquot. Some experimentation to establish optimum times may be necessary on the part of the operator, once the other stressor levels have been set. Under most stressor conditions, preferred times will be in the approximate range of from about 2 to about 5 minutes, more preferably about 3 minutes. The starting blood temperature, and the rate at which it can be warmed or cooled to a predetermined temperature, tends to vary from subject to subject. Preferably four such lamps are used.

In the practice of the preferred process of the present invention, the blood aliquot may be treated with the stressors using an apparatus of the type described in aforementioned U.S. Pat. No. 4,968,483 to Mueller. The aliquot is placed in a suitable, sterile, UV light-transmissive container, which is fitted into the machine. The UV lamps are switched on for a fixed period before the gas flow is applied to the aliquot providing the oxidative stress, to allow the output of the UV lamps to stabilize. The UV lamps are typically on while the temperature of the aliquot is adjusted to the predetermined value, e.g. 42.5±1° C. Then the oxygen/ozone gas mixture, of known composition and controlled flow rate, is applied to the aliquot, for the predetermined duration of up to about 60 minutes, preferably 2 to 5 minutes and most preferably about 3 minutes as discussed above, so that the aliquot experiences all three stressors simultaneously. In this way, blood is appropriately modified according to the present invention to achieve the desired effects.

In operating the process of the invention, it is preferred to give a patient a course of treatments, comprising a daily or alternate day treatment, over a period of one or two weeks. Each treatment is substantially identical, with the same volume aliquot being extracted, stressed and re-injected. The course of treatments is scheduled to be completed shortly before the patient is to be exposed to an apoptosis-accelerating factor as described above, for most effective preconditioning against the effects thereof.

The invention is further illustrated and described with reference to the following specific examples, namely animal studies conducted in approved manner.

The experiments reported in the examples demonstrate, by use of an animal model system involving ischemia and subsequent reperfusion of various body organs, that the process of the present invention has the effect of reducing apoptosis and necrosis. Ischemia-reperfusion injuries are known to involve increase of apoptosis and necrosis in the affected organs and tissues—see for example Saikumar p, et. al. "Mechanisms of cell death in hypoxia/reoxygenation injury", *Oncogene* 1998 Dec. 24; 17(25):3341–9; and Burns A. T. et. al., "Apoptosis in ischemia/reperfusion injury of human renal allografts", *Transplantation,* 1998 Oct. 15; 66(7): 872–6, and other publications both preceding and following those. Known techniques of determination of apoptosis at the cellular level are employed in the examples. The finding that the process of the invention decreases apoptosis and necrosis in this model is indicative of its utility in the various categories of apoptosis-associated disorders discussed above.

EXAMPLE 1

Pure-bred normal beagle dogs, aged 1–2 years, equal numbers of males and females, were used as the experimental animals. The animals were separated into four groups, A, B, C and D, each group consisting of six animals, three males and three females. Animals of groups A and C were subjected to the process of the invention, by being subjected to two 10-day courses of daily removal of an 8 ml aliquot of blood, extracorporeal treatment of the aliquot with oxygen/ozone, UV radiation and heat, and re-administration of 5 ml of the treated aliquot to the same animal, by intramuscular injection.

Each such treatment was conducted as follows.

An 8-ml aliquot of blood was extracted from the animal, treated with sodium citrate (2 ml) and placed in a sterile container. It was subjected simultaneously to the UV radiation, oxygen ozone gas oxidative environment and elevated temperature stressors, m an apparatus as generally described in the aforementioned Mueller U.S. Pat. No. 4,969,483. More specifically, the blood sample in the sterile, UV-transparent container was heated using infra-red lamps to 42.5° C., and whilst being maintained at that temperature, it as subjected to UV radiation of wavelength 253.7 nm under the preferred conditions previously described. Simultaneously, a mixture of medical grade oxygen and ozone, of ozone content 13.5–15.5 ug/ml was bubbled through the blood sample at a flow rate within the range from 60–240 mls/min. The time of simultaneous UV exposure and gas mixture feed was 3 minutes. A 5 ml portion of the treated blood aliquot was reinjected intramuscularly into each test animal.

Each animal of groups A and C, receiving the courses of treatment according to the mls/min, experienced a three week rest period between the 10-day courses of treatment. Groups B and D were the control groups, given two 10-day courses of daily injections of 5 ml of physiological saline, with a three-week rest period between the 10-day courses.

One day following the second course of injections, the animals were anaesthetized under, light gas anaesthesia, and the right kidney of each animal was removed through aback incision. An occlusive clip was placed on the remaining renal artery and vein, to expose the left kidney to transient ischemia, for 60 minutes. Then the clip was removed to allow reperfusion of the kidney by normal blood flow.

The animals were observed for 6 days after the ischemia procedure, and then sacrificed. The ischemic kidney of each animal was surgically removed and divided into two parts. One part was kept frozen at −80° C., and the other part was fixed in 10% formalin for immuno- and routine histopathology studies.

Mitochondrial membrane potential was measured in proximal tubular cells isolated from the ischemic and control kidneys, both at the time of removal of the control kidney and following sacrifice. For this purpose, dog kidney proximal tubes were purified from normal or ischemic kidney cortexes by the collagenase treatment procedure described by Marshansky et. al., "Isolation of heavy endosomes from dog proximal tubes in suspension", J. Membr. Biol 153(1), 59–73, 1996. Renal mitochondria were isolated in suspension by differential centrifugation (see Marshansky, "Organic hydroperoxides at high concentrations cause energization and activation of AATP synthesis in mitochondria", J. Biol. Chem. 264(7), 3670–3673, 1989, after tissue homogenization in a buffer containing 250 mM sucrose, 10 mM HEPES-Tris (pH 7.5), and 250 µM EDTA. Cell debris was removed by centrifugation at 10,000 g for 30 minutes. The mitochondria were washed with the sucrose/HEPES buffer without EDTA.

Mitochondrial membrane potential was measured as described by Kroemer, G., Zamzam, N. and Susin, S. A., "Mitochondrial control of apoptosis", (Review) Immunology Today (1997) v.18, p 44–51; with JC-1 dye—see Salvioli et.al., "JC-1, but not DiOC6(3) or rhodamine 123, is a reliable fluorescent probe to assess delta psi changes in intact cells: implications for studies on mitochondrial functionality during apoptosis", FEBS Letters 411 (1), 77–82, 1987. JC-1 fluorescence in the suspension of purified mitochondria from normal and ischemic kidneys was monitored continuously on a Deltascan Model RFM-2001 spectrofluorimeter (Photon Technology International, South Brunswick, N.J.). The excitation wavelength was 490 nm (slit width 2 nm) and the emission wavelength was 590 nm (slit width 4 nm). The signals were recorded using Felix® (Version 1.1) software. All measurements were performed with continuous stirring at 37° C. The incubation buffer for measurement of mitochondrial membrane potential contained 200 mM sucrose, 5 mM $MgCl_2$, 5 mM $KH_2PO_4$, 0.1µM of JC-1 and 30 Mm HEPES-Tris (pH 7.5). The concentrations of the substrate and inhibitors were 10 mM succinate, 0.1 µM rotenone with or without 0.1 µM FCCP. Proximal tubule mitochondrial membrane potential was estimated in the right (control) kidney prior to ischemia and in the left (ischemic) kidney after sacrifice of the dogs on day 6 following ischemia and was estimated as difference of JC-1 fluorescence after uncoupling of mitochondria with FCCP as shown in the accompanying FIG. 1A. For each measurement, 50 µ g protein of purified material was used.

JC-1 fluorescence is proportional to the mitochondrial membrane potential. The contralateral nephrectomized kidney served as control. As is clear from the FIG. 1B, the treatment process of the invention did not modify the membrane potential of the non-ischemic control night kidney ($p=0.445$ for treated vs saline). However, the ischemic kidney of the saline-injected animals showed significantly lower ($p<0.05$) fluorescence compared to the control kidney. The stress treatment according to the invention prevented the uncoupling of mitochondria during ischemic/reperfusion, and membrane potential showed no significant difference ($p=0.244$) between ischemic and control kidneys. This parameter remained significantly higher ($p=0.0006$) vs saline-injected dogs) in the ischemic kidneys of dogs pretreated according to the process of the invention for at least 6 days post-reperfusion.

These results indicate that the process of the invention effects protection of the kidney against apoptosis and/or accelerates recovery at the mitochondrial level. Accordingly the process of the invention is indicated for pre-conditioning of the cells, tissues and organs of a mammalian body against subsequently encountered factors which will normally accelerate apoptosis.

Specifically, the preservation of mitochondrial membrane potential evidences the capacity of the therapy to protect mitochondria, and thereby to precondition cells against apoptosis.

EXAMPLE 2

A group of 12 male SHR rats was treated with either injections of pooled blood stressed as described in Example 1 above, or, in control animals, with injections of saline. Since the blood from all of the animals of this genetic strain is identical, blood from one animal of this same strain was treated by the process of the invention for administration to the test animal. The blood was treated with sodium citrate as anti-coagulant, and placed in a sterile container They received either injections of 150 µl of stressed blood on days—14 and—13 followed by a rest period of 11 days and a third injection the day before ischemic surgery, or injections in parallel with saline. On the day of surgery, the rats were anaesthetized with light flurane, and the right kidney was removed through a mid-abdominal incision. The left kidney was then subjected to transient ischemia by occlusion of the left renal artery and vein using a micro-clip. The skin was then temporarily closed. After 60 minutes of occlusion, the clip was removed and the wound was closed with a suture. The animals were sacrificed 12 hours after reperfusion.

The ischemic and non-ischemic kidneys of the test animals were removed and subjected to DNA laddering tests. Oligonucleosomal DNA fragmentation into 180 to 200 base pairs is a specific pattern which appears as a ladder after agarose gel electrophoresis in various organs undergoing apoptosis. To estimate the degree of DNA fragmentation in the kidney cortex, an aliquot of pulverized kidney cortex was weighed and total tissue DNA was extracted by the phenol-chloroform procedure after tissue digestion with proteinase K and RnaseA in the presence of EDTA. One µg of extracted DNA was labeled by enzymatic assay using terminal deoxynucleotidyl transferase with $^{32}$-dCTP (see Teiger et.al., 'Apoptosis in pressure overload-induced heart hypertrophy in the rat', J. Clin. Invest. 97, 2891–2897, 1996). Increasing quantities of radio-labelled DNA were loaded onto 1.5% agarose gels. After electrophoresis, DNA was transferred onto nylon membranes (Hybond) and the radioactivity associated with 150 to 1500 bp DNA fragments was quantified in a PhosphorImager (Molecular Dynamics). A regression line for each sample was drawn for the radioactivity as a function of DNA loaded on the gel (see deBlois et.al., 'Smooth muscle cell apoptosis during vascular regression in spontaneously hypertensive rats.' Hypertension 29, 340–349, 1997). The slope of the linear regression line served as a DNA fragmentation index (cpm/pixel per µg DNA).

Figure 2:
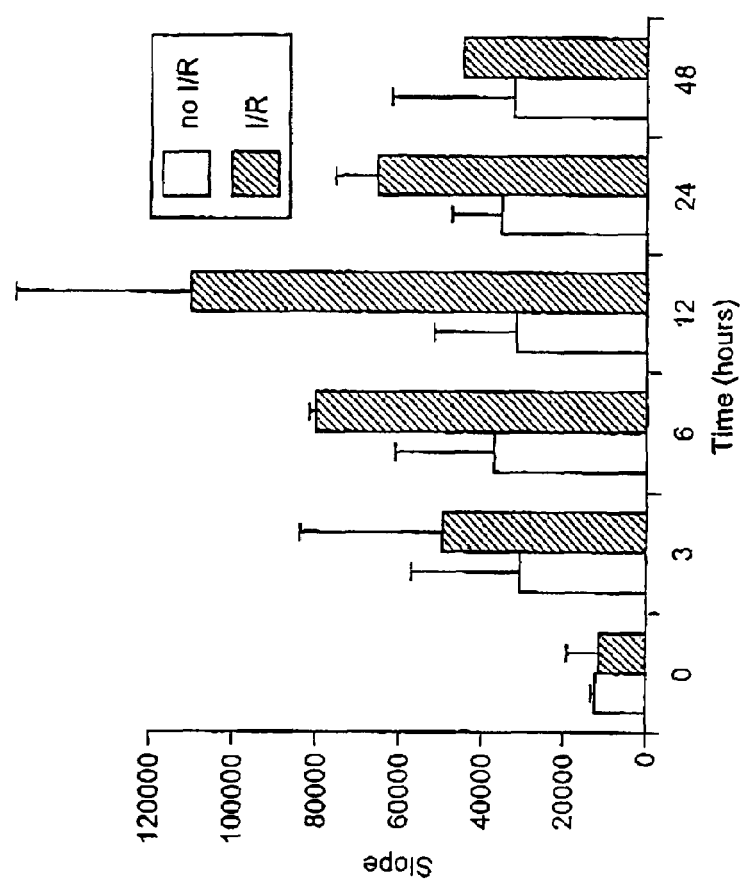
FIGS. 2 and 3 of the accompanying drawings are graphical presentations of the results obtained from Example 2 described below.

The results from ischemic-reperfused (I/R) kidneys and from normal, non-I/R kidneys, all from animals which did not receive injections of stressed blood, are shown graphically on FIG. 2, a plot of the slope of the regression lines for the various samples (vertical axis) against time after initiation of reperfusion. The DNA laddering, indicative of DNA fragmentation, was clearly increased in the ischemic kidney cortex compared to the contralateral non-ischemic organ and the maximal attained at twelve hours returned to near basal values by 48 hours. Twelve hours was thus selected as the time point for study of the effect of the stressed blood of the invention on early ischemia-induced renal apoptosis.

Figure 3:
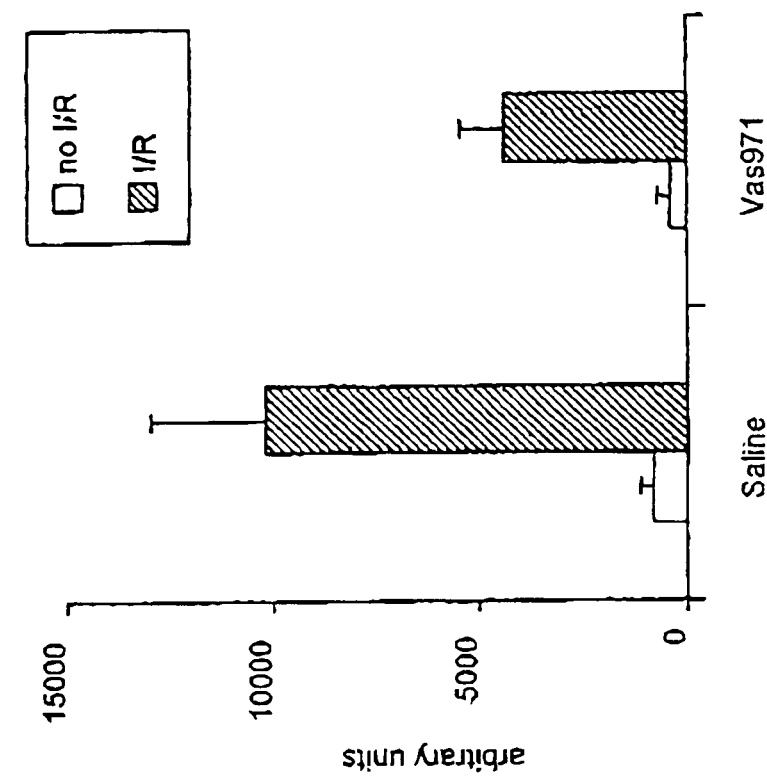
Figure 3:
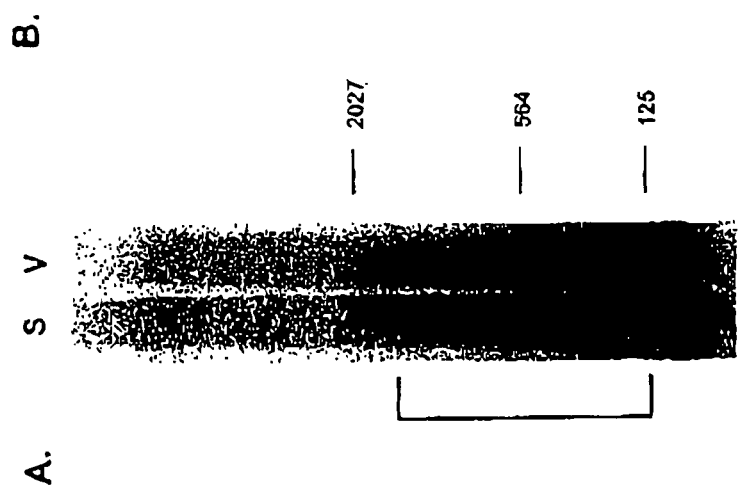

FIG. 3A of the accompanying drawings is a picture of the electophoresis gel of the fragmented DNA, in the 150–1500 bp range, radio-labeled as described to attach radioactivity labels to the DNA-fragments. Trace S derives from DNA of kidneys from animals which received saline injections prior to kidney ischemia-reperfusion, and trace V derives from DNA of kidneys of animals which received injections of the stressed blood, prior to kidney ischemia-reperfusion. The Figure shows that 60 minutes renal ischemia induced a clear accumulation of fragmented DNA in both groups of rats at 12 h but the level of this parameter was significantly lower ($p<0.05$) in animals receiving the treated blood. FIG. 3B quantifies the amount of irradiation from the samples, in arbitrary units, and shows that DNA fragmentation-laddering occurs in both S and V samples as a result of ischemia/reperfusion but that the extent is markedly reduced in V samples as compared with S samples. The results presented on FIG. 3B are the means of six animals in each case.

These results confirm that the cytoprotective effect of the administration of stressed blood according to the invention on renal reperfusion injury involves the inhibition of early or late apoptosis.

EXAMPLE 3

Heart Studies—Protection of Removed Organs

Experiments were carried out in rats, more specifically in male Sprague-Dawley rats to demonstrate the protection of removed organs, deprived of the donor's blood, against a sustained ischemic insult as typically observed with classical ischemic preconditioning protocol (K. Przylenk and R. A. Kloner, Progress in Cardiovasc. Dis. vol 40: 517–547, 1998).

Two groups of four rats, 270–285 g body weight, were used. One group of rats (n=4) received a saline injection and served as controls. The other group of rats received blood treated by a protocol in accordance with the invention. Since the blood from all of the animals of this genetic strain is identical, blood from one animal of this same strain was treated by the process of the invention for administration to the test animal. The blood was treated with sodium citrate as anti-coagulant, and placed in a sterile container. It was heated and subjected simultaneously to the UV stressor and oxygen/ozone stressor in the amounts and under the conditions set out in Example 1 above.

Each test animal received on day 1 an injection of 150 µl of the treated blood, followed by a 10-day rest period. Then each animal received a 150 µl injection of treated blood on both day 12 and on day 13. Each control animal received similar injections, on the same schedule, of physiological saline. The animals were then sacrificed on day 14.

From each animal, the heart was removed and perfused ex vivo according to the Langendorf mode with non-recirculating Krebs Henseleit buffer gassed with 95% oxygen/5% carbon dioxide pH 7.4, containing glucose as energy substrate. The heart was submitted to an ischemia-reperfusion insult as typically is used in studies of cardiac ischemic preconditioning (see for example R. T. Rowland et. al., Am. J. Physiol. 272, H2708–H2715; E. O. Weselcouch et. al., Cardiovasc. Res. 29; 126–132, 197). Briefly, after a 20 minute equilibration period under normoxia, the heart was submitted to a 25 minute global ischemia at 37° C. Then, it was reperfused for 45 minutes as follows: (i) for the initial 25 min of reperfusion, the heart was allowed to beat spontaneously, the (ii) it was paced using pacing wires fixed to the right atrium to achieve a rhythm of 300 beats/min.

Figure 4:
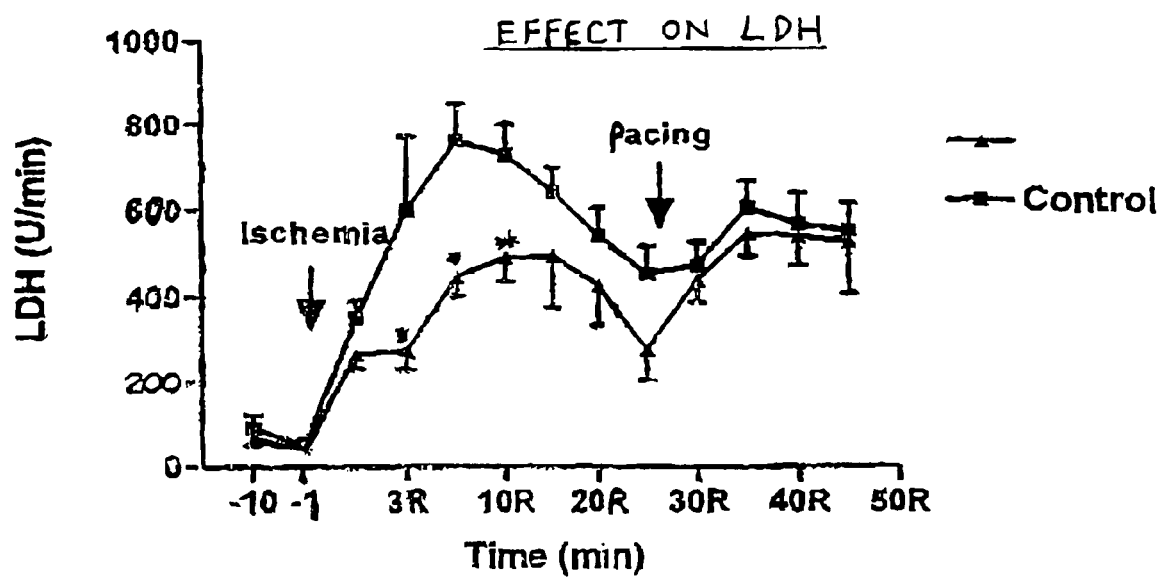
FIG. 4 of the accompanying drawings is a graphical presentation of the results obtained according to Example 3 below.

FIG. 4 indicates data measuring the perfusion protocol for the lactate dehydrogenase released into the effluent perfusate, an index of cellular necrosis, as evaluated by a standard enzymatic assay. In FIG. 4 of the drawings, the curve based on the triangular-form points is derived from organs of animals which received blood treated with stressors as described. The curve based on square-form points is derived from the organs of the control animals which received saline solution. FIG. 4 indicates a significant reduction in LDH release (cumulative LDH release during the 45 minute reperfusion period; $p<0.05$; treated vs saline), indicative of significantly reduced cell necrosis in organs treated with stressor as described.

What is claimed is:

1. A method for treating the symptoms of a neurological medical disorder mediated by accelerated rates of apoptosis in a mammalian body, which method comprises:
   (a) selecting a patient having or suspected of having a neurological medical disorder mediated by accelerated rates of apoptosis;
   (b) reacting an aliquot of blood from the mammalian body of said patient ex vivo with a stressor comprising both:

an oxidative environment stressor wherein the oxidative environment is selected from the group consisting of liquid and gaseous oxidizing agents wherein the gaseous oxidizing agent is a mixture of ozone and medical grade oxygen; and an ultraviolet light stressor;

and optionally a temperature stressor which is a temperature above or below body temperature;

and (c) administering the aliquot of blood treated in step (b) to the mammalian body; thereby reducing the rate of apoptosis.

2. The method of claim 1 wherein the aliquot of blood has a volume from about 0.1–100 ml.

3. The method of claim 2 wherein when the temperature stressor is employed said stressor is a temperature in the range from about −5° to 55° C.

4. The method of claim 2 wherein said temperature stressor is a temperature in the range of from about 40° to 50° C.

5. The method of claim 2 wherein said oxidative environment stressor comprises a mixture of ozone and medical grade oxygen, bubbled through the blood aliquot.

6. The method of claim 5 wherein the gaseous mixture has an ozone content of from about 10–100 μg per ml.

7. The method of claim 2 wherein said ultraviolet light stressor is ultraviolet light in the UV-C band wavelength.

8. The method of claim 2 wherein all three stressors are applied to the aliquot simultaneously.

9. The method of claim 8 wherein said stressors are applied for a period of time from 0.5 to 60 minutes.

10. The method of claim 9 wherein the time is from about 2 to 5 minutes.

11. The method of claim 1, wherein the neurological disorder is Parkinson's disease, senile dementia or Alzheimer's disease.

* * * * *

UNITED STATES PATENT AND TRADEMARK OFFICE
CERTIFICATE OF CORRECTION

PATENT NO.       : 7,045,124 B1
APPLICATION NO.  : 09/480260
DATED            : May 16, 2006
INVENTOR(S)      : Pavel Hamet et al.

It is certified that error appears in the above-identified patent and that said Letters Patent is hereby corrected as shown below:

On Title Page, Col. 1

At field (75) Inventors:

Replace "Johannes Tremblay" with -- Johanne Tremblay -- and

Replace "Christine Desrosier" with -- Christine Des Rosiers --

Signed and Sealed this

Nineteenth Day of September, 2006

JON W. DUDAS
*Director of the United States Patent and Trademark Office*